United States Patent [19]
Del Campo

[11] 4,158,683
[45] * Jun. 19, 1979

[54] PROCESS FOR OBTAINING FILMS AND BLOCKS OF CELLULOSE ACETATE PARTICULARLY FOR RAPID AND PREPARATIVE ANALYTICAL ELECTROPHORESIS AND FOR IMMUNO-TECHNIQUES

[76] Inventor: Giovan B. Del Campo, Via Gustavo Modena, 24, Milan, Italy, 20129

[*] Notice: The portion of the term of this patent subsequent to Jan. 21, 1992, has been disclaimed.

[21] Appl. No.: 355,994

[22] Filed: Apr. 30, 1973

Related U.S. Application Data

[63] Continuation-in-part of Ser. No. 70,897, Sep. 9, 1970, abandoned.

[30] Foreign Application Priority Data

Apr. 28, 1970 [IT] Italy ................. 24029 A/70

[51] Int. Cl. ................................ B29d 7/02
[52] U.S. Cl. ...................... 264/41; 210/500 M; 264/49; 264/216; 264/217
[58] Field of Search .................. 264/41, 49, 216, 217

[56] References Cited

U.S. PATENT DOCUMENTS

| 2,926,104 | 2/1960 | Goetz ................. 264/217 |
| 3,344,214 | 9/1967 | Manjikian et al. ........ 264/217 |
| 3,412,184 | 11/1968 | Sharples et al. .......... 264/41 |
| 3,432,584 | 3/1969 | Cannon et al. ........... 264/41 |
| 3,432,585 | 3/1969 | Watson et al. ........... 264/49 |
| 3,497,072 | 2/1970 | Cannon ................. 264/217 |
| 3,567,809 | 3/1971 | Ueno et al. ............. 106/189 |
| 3,592,672 | 7/1971 | Rowley et al. ........... 210/500 |

OTHER PUBLICATIONS

Manjikian et al., "Improvement in Fabrication Techniques for Reverse Osmosis Desalination Membranes," First International Symposium on Water Desalination, Oct. 3–9, 1965, Washington, D.C., pp. 1–6 & 13.

Primary Examiner—Ronald W. Griffin
Attorney, Agent, or Firm—Guido Modiano; Albert Josif

[57] ABSTRACT

An improved process for preparing films and blocks consisting essentially of cellulose diacetate aqueous gel, which are suitable for electrophoresis purposes, which process comprises dissolving cellulose diacetate in a first mixture of a major proportion of a water-miscible solvent with a minor proportion of a water-miscible swelling agent; swelling the cellulose diacetate solution by adding a second mixture of a major proportion of the swelling agent with a minor porportion of the solvent; adding to the swollen mass an amount of from 3 to 10% by weight based on the swollen mass of formamide, as regulator of the water content of the aqueous gel, substituting in the swollen mass water for the solvent and the swelling agent and casting the aqueous gel thus obtained to form a film or block by means of conventional procedures; wherein each of the foregoing steps is carried out at room temperature.

2 Claims, No Drawings

PROCESS FOR OBTAINING FILMS AND BLOCKS OF CELLULOSE ACETATE PARTICULARLY FOR RAPID AND PREPARATIVE ANALYTICAL ELECTROPHORESIS AND FOR IMMUNO-TECHNIQUES

CROSS-REFERENCE TO RELATED APPLICATIONS

This application is a continuation-in-part of applicant's copending application, Ser. No. 70,897, filed Sept. 9, 1970, now abandoned.

BACKGROUND OF THE INVENTION

1. Field of the Invention

This invention relates to an improved process for obtaining films and blocks of cellulose acetate, particularly but not exclusively suitable for rapid and preparative analytical electrophoresis and for immuno techniques. More specifically, this invention relates to an improved process for obtaining films and blocks which are suitable for the above mentioned electrophoresis purposes, which consist essentially of cellulose diacetate aqueous gel. This invention also relates to blocks and films of cellulose diacetate aqueous gel obtained by said process.

2. Description of the Prior Art

Cellulose acetate membranes (or films) and processes for their preparation have been known long since. The membrane structure and composition and, consequently, their manufacture methods differ widely, however, depending on the membrane end use. The main fields of cellulose acetate membrane application are waste water purification by the reverse osmosis method and analytical electrophoresis.

It should be clearly understood that a cellulose acetate membrane which is successfully suitable for reverse osmosis purposes is not suitable at all for electrophoresis purposes, and vice versa.

The reverse osmosis membranes (or "semipermeable" membranes) formed from cellulose acetate, posses the unique capability of allowing the passage of pure water at reasonably high throughput rates, while rejecting a large percentage of the water-pollutants. The most accepted and experimentally supported theory for the perm-selectivity of the cellulose acetate reverse osmosis membrane suggests that the membrane is composed of a dense "skin," which is only about 0.25 microns in thickness, supported by a porous structure. This dense skin, which would be responsible for the perm-selectivity of the membrane, is composed of crystalline and amorphous zones. In the crystalline zones, the internal stresses restrict the motion of the cellulose biacetate polymer chains. Because of these crystalline zones, the intermolecular distances in the amorphous zones are much smaller than would be expected if there are no crystalline zones.

When the water molecules contact the membrane skin, they concentrate in the amorphous zones whereby they cross-link by hydrogen bonds the cellulose acetate polymer chains. A "pore" in the skin may therefore be envisioned as a small amorphous zone wherein the crosslinking is complete, leaving no "holes" through which ions, which are relatively larger than water molecules, can pass. Water molecules only will be therefore transported across the skin by what is termed "alignement type diffusion" where hydrogen bonds are broken and restored while a water molecule is driven across the skin by pressure differential. The production of cellulose acetate perm-selective membranes is similar to casting procedure for most solvent cast films, except but two essential features. First, the membrane casting solution contains a suitable agent to control membrane porosity, since—as previously indicated—the pores of the skin have to be small enough to prevent the passage of any molecule but water. Second, the membrane is subjected to an annealing step which is usually carried out at temperatures of from about 70° to 85° C. The purpose of the annealing step is, as disclosed for instance in the British Pat. No. 1,159,218 (issued to Aerojet-General Corporation): "to provide a tight membrane having the ability to pass water and restrain passage of salt. During the annealing process a contraction of the swollen gel structure is accomplished. Prior to annealing, the swollen cellulose ester membrane possesses a primary gel structure which exhibits high water transport and low salt retention. Annealing is a syneresis phenomenon, wherein the primary gel structure is shrunk as evidenced by loss of water from the membrane. Annealing may be achieved by immersion of the swollen primar gel structure in a hot water bath."

As disclosed by Manjikian S. et al. ("Improvement in fabrication techniques for reverse osmosis desalination membranes"—First International Symposium on Water Desalination, Oct. 3–9, 1965 Washington D.C.) aqueous magnesium perchlorate was originally included in the casting solution as one of the steps to control reverse osmosis membrane porosity, which was later substituted by formamide as a replacement for both water and magnesium perchlorate, the range of casting solution studied by the foregoing authors being cellulose acetate 20–30 wt.%, formamide 10–40 wt.%, acetone 35–65 wt.%.

The cellulose acetate films suitable for electrophoresis purposes are extremely different from the reverse osmosis membranes particularly as far as the porosity of those materials is concerned. In fact, far from possessing any superficial skin of the afore-mentioned type which allows the passage of the small water molecules only, a material suitable for electrophoresis purposes must have pores of a relatively large diameter to permit the penetration of large organic molecules to be analysed, as for instance hemoglobin whose molecular weight is many thousand times that of water.

These films are commercially available in the form of thin microporous, dry, re-wettable strips with pore sizes up to a diameter of 5 microns, i.e., with pores which are greater than the molecular dimensions of the substances to be analysed by means of electrophoresis. Films of conventional type are moreover produced with thicknesses comprised between 110 and 200 microns only and therefore they are confined to the micro-electrophoretic analysis of highly concentrated samples.

Although these films are advantageous from some points of view, they give rise to other considerable disadvantages which are summarised hereinafter:

1. During immersion in aqueous baths they may trap air in the micropores.

2. Films exposed to air completely lose the water of impregnation in about 30 minutes at a temperature of 20° C. Moreover after a few moments of exposure to air said films lose water to the point of showing clear white spaces when it is well known that for practical use a large capacity for retaining water is required.

3. The films present different characteristics of solubility in solvents according to the degree of acetylation of the starting material, while easy solubility in solvents miscible with water such as acetone is required, together with easy attack by transparentising solvents such as acetic acid.

4. The relatively limited thickness of the films at present available commercially does not allow large volumes of samples to be deposited and analysed, while for unlimited use of electrophoresis the ability to analyse liquids with small concentrations of components in large volumes is required.

5. The relatively large size of the pores of the films at present available on the market may oppose electrophoretic separation because the components of the substance to be analysed spread to a point that they overlap and become confused during the time of electrophoresis. Moreover losses of substances can arise during post-electrophoresis treatments because of flow from the pores.

6. Films at present available in commerce in the dry state are very fragile.

To control pore diameter up to those dimensions which are required by the electrophoretic intended use and reduce film fragility, which constitutes a major problem in the dry, re-wettable cellulose acetate film production, Ueno et al. (U.S. Pat. No. 3,567,809) have disclosed a method which comprises subjecting a film consisting of a mixture of cellulose diacetate and triacetate to a first drying step at a temperature of from 15° C. to 45° C. and a second drying step at a temperature of from 80° C. to 120° C., wherein a plasticizer of suitable hydrophobicity is used.

Finally, methods for producing films of cellulose ester aqueous gel are also known, which generally comprise dissolving a film-forming cellulose ester and a swelling agent in an organic solvent, casting the solution thus obtained to form a film, evaporating at least portion of the organic solvent from the cast film and immersing the cast film in water to substitute water for the organic solvent. These methods are generally unsatisfactory, because it is not possible to regulate the water content of the aqueous gel. As is well known to any expert in the electrophoretic methods and techniques, because of the Joule effect caused by the electric current flowing through the film, an insufficient content of water present within the gel structure may result in an excessively fast drying of the film, which might ultimately cause inaccuracies in the analysis results. Besides, the water molecules linked by hydrogen bonds to cellulose ester polymer chains, affect the movement of high molecular weight molecules to be analysed.

SUMMARY OF THE INVENTION

It is an object of my invention to provide an improved process for producing films and blocks suitable for electrophoresis purposes, which consist essentially of cellulose biacetate aqueous gel containing a controlled amount of water within the gel structure.

According to my invention, the improved process for obtaining films and blocks consisting essentially of cellulose diacetate aqueous gel, particularly suitable for rapid and preparative analytical electrophoresis and for immunotechniques, comprises dissolving a starting load of cellulose diacetate in a first mixture comprising a major proportion of a water-miscible solvent and a minor proportion of a water-miscible swelling agent for said cellulose diacetate; adding under stirring to the cellulose diacetate solution thus obtained a second mixture comprising a minor proportion of a water-miscible solvent and a major proportion of a water-miscible swelling agent for said cellulose biacetate, thereby obtaining a swollen mass; adding under stirring to said swollen mass an amount of formamide in the range of from 3 to 10% by weight based on said swollen mass; casting said swollen mass to form a film or block; evaporating at least a portion of said solvent, and immersing the cast film or block in water, thereby substituting in the cast film or block said solvent and swelling agent by water, thus obtaining the cellulose diacetate aqueous gel; and wherein each of foregoing steps is carried out at room temperature.

DESCRIPTION OF THE SPECIFIC EMBODIMENTS

My invention is based on the discovery, which appears to be surprising in view of the above-mentioned use of formamide as a replacement for water and magnesium perchlorate in the preparation of reverse osmosis membranes, that formamide acts as a regulator of the water content within the gel structure of cellulose diacetate aqueous gel suitable for electrophoresis purposes. It is particularly surprising that, although in reverse osmosis membrane manufacture, formamide is used to control membrane porosity down to those minute diameters allowing the passage of pure water while rejecting a large percentage of the impurities, formamide does not affect the porosity of a cellulose diacetate aqueous gel prepared in accordance with my invention. On the contrary, the aqueous gel of my invention permits the penetration and movement of very high molecular weight molecules, as required by the electrophoretic intended use of these materials, while, by varying the amount of formamide added to a swollen mass of cellulose diacetate, it is possible to regulate within wide limits the water content within the ultimate gel structure. I will hereafter refer for convenience's sake to the "water content within the ultimate gel structure" as the "water of constitution" of the gel, although no theory is being formulated on the structural relationship between water and cellulose diacetate. Water molecules, however, are likely to be linked to cellulose diacetate polymer chains by means of hydrogen bonds.

I have found that the water of constitution of a cellulose diacetate aqueous gel highly suitable for electrophoresis purposes, can be varied within wide limits, i.e., between about 60 and about 75% by weight based on overall weight of the aqueous gel, by adding an amount of formamide of from 3 to 10% by weight based on the weight of a swollen mass which is obtained by dissolving a starting load of cellulose diacetate in a first mixture comprising a major proportion of a water-miscible solvent and a minor proportion of a water-miscible swelling agent for the cellulose diacetate, and then adding under stirring to the solution a second mixture comprising a minor proportion of the solvent and a major proportion of the swelling agent.

Preferably, acetone is used as the solvent for the cellulose diacetate and ethylene-glycol-monoethyl ether as the swelling agent.

The ratio by volume of acetone to ethylene-glycol-monoethyl ether is preferably 3:2 in said first mixture and 1:5 in said second mixture.

Further characteristics and advantages of the process according to the invention will be more evident from the detailed description of some preferred but not exclusive embodiments thereof illustrated in the following examples.

EXAMPLE 1

Preparation of Films of Cellulose Diacetate Aqueous Gel.

One hundred grams of 56% acetic acid cellulose acetate (i.e., cellulose diacetate) were dissolved under stirring for one night in a first mixture consisting of 300 cc of acetone and 200 cc of ethylene glycol monoethyl ether. Into this mixture kept under stirring, a second mixture consisting of 100 cc of acetone and 500 cc of ethylene glycol monoethyl ether was dripped, taking care to avoid the formation of clots, thus obtaining a swollen mass. Agitation was maintained for about 1.5 hours while an amount of from 3 to 10% by weight based on the swollen mass, of formamide was added.

At the end of agitation, filtration was carried out and the mass was extended in the form of a film of required thickness.

This film was conditioned for about 30 minutes in low pressure surroundings in order to favour the evaporation of the acetone and was then immersed in water to substitute the remaining acetone and the ethylene glycol monoethyl ether. The material thus obtained was then cut and packaged in the humid state.

By this process translucent, white films are obtained. These films on exposure to air begin to dry after 10 minutes and their dimensions reduce after some hours by 10% with respect to the initial dimensions. These products have degree of gelatinisation controlled by the quantity of formide added to the mixture.

For instance, 3%, 10% and 20% of formamide were respectively added to the foregoing swollen mass and the corresponding products thus obtained were further processed and casted into films as previously indicated. Three strips each of a 14 cm length, 2.5 cm width and 220 micron thickness were thus produced. These films exhibited the following charactistics:

| Film characteristics | Formamide content | | |
|---|---|---|---|
| | 3% | 10% | 20% |
| Total water (+) (i.e. water of imbibition + water of constitution) | 91,5% | 92% | 92,5% |
| Water of imbibition (i.e. amount of water lost after 30 minutes of exposure to air) | 26,5% | 20% | 11.5% |
| Water of constitution (i.e. total water − water of imbibition) | 65% | 72% | 81% |
| Film weight after 12-hour exposure to air (mg) | 102 | 105 | 103 |
| Length decrease after 30-minute exposure (mm) | 1 | 5 | 7 |
| Length decrease after 12-hour exposure (mm) | 10 | 40 | 70 |
| Dried film appearance | white, microporous, curled | white, crystalline, curled | semi-transparent, crystalline, fragile, curled |

(+) Total water percentage is expressed by the following formula:
$$\frac{\text{Initial humid film w.} - \text{Film w. after 12-hour exp. to air}}{\text{Initial humid film weight}} \times 100$$

It has been noted that, by increasing the formamide content over 20% based on the swollen mass, rubber-like films no more suitable for electrophoresis purposes are obtained. In fact these films markedly shrink and curl up after only few minutes of exposure to air.

EXAMPLE 2

Preparation of Blocks of Cellulose Diacetate Aqueous Gel.

The procedure of Example 1 was followed (10% by weight of formamide based on the swollen mass was added), except that the swollen mass was poured on a glass plate having a rubber frame of suitable thickness (for instance: 5 mm). The assembly was then immersed in water to substitute water for ethylene-glycol-monoethyl ether and acetone.

In using the above mentioned process, it has been noted that the swelling agent of the starting cellulose acetate used (i.e., ethylene glycol monoethyl ether) has the property of regulator of the pores and molecular structure of the final product; i.e., it gives a uniformity of structure to the product contrary to other swelling agents which could be utilised, for example ethyl alcohol. Ethyl alcohol leads to the obtaining of a product whose molecular orientation and final structure are not uniform.

The products obtained by carrying out the process of this invention as exemplified above, either in the form of films or blocks of cellulose acetate in a humid state, lead to the attainment of the following advantages:

1. The humid film does not give rise to problems of impregnation with air bubbles when it is immersed in a liquid bath.

2. When exposed to air the humid films do not dry easily because the cellulose acetate in the gel state has a very strong capacity for retaining water. This allows an increased range of electrophoretic applications and also allows other gels such as agar-gel in immunodiffusion techniques to be substituted by the gelatinised cellulose acetate of this invention.

3. The films are easily soluble in the solvents of cellulose diacetate and readily become transparent after a bath in a dilute solution of for example acetic acid. They can also be produced in the semi-transparent state in which case no special treatment is required.

4. As large thicknesses can be produced with the films obtained by the processes of this invention, it is possible to analyse samples of very low concentration without limiting the electrophoresis to highly concentrated samples. Consequently it is possible to apply the humid cellulose acetate of this invention to preparative electrophoresis.

5. The limited porisity and gel state of the film avoids spreading the substances under examination during the electrophoresis time and avoids loss of components during post-electrophoretic treatment.

6. No fragility problem exists because the gelatinised films can be bent through 360° without breaking.

Advantageously the products obtained by the process of this invention may be packaged and sold in the following manner:

(A) Films of gelatinised cellulose acetate of translucent appearance (high degree of gelatinisation) of thickness 250 microns, cut into strips and packaged in the humid state in a glass jar in a solution of water and anti-mildew compound or water and methanol.

(B) Films of gelatinised cellulose acetate of white non-translucent appearance of thickness 300 microns, cut into strips or sheets and packaged in plastic sealed envelopes containing water and anti-mildew compound or water and methanol in them.

(C) Blocks of gelatinised cellulose acetate of white spongy appearance of thickness 5 mm cut into rectangles, e.g., 6×17 cm packaged in the humid state in a plastic packet containing water and methanol.

(D) A film of gelatinised cellulose acetate of white appearance of thickness 220–240 microns, cut into strips 5×23 cm with for example a V-shaped cross-section (wedge strip) packaged in the humid state.

Having thus described my invention, what it is desired to secure and claim by Letters Patent is:

1. In a process for preparing films and blocks suitable for electrophoresis purposes, consisting essentialy of cellulose diacetate aqueous gel, which process comprises dissolving the cellulose diacetate in acetone, casting the solution thus obtained to form a film, evaporating at least a portion of said acetone, and immersing the cast film in water, the improvement which comprises varying the water content of the aqueous gel by dissolving said cellulose diacetate in a first mixture comprising acetone and ethylene-glycol-monoethyl ether in a ratio by volume of about 3:2; adding under stirring to the cellulose diacetate solution a second mixture comprising acetone and ethylene-glycol-monoethyl ether in a ratio by volume of about 1:5, thereby obtaining a swollen mass; adding under stirring to said swollen mass an amount of formamide in the range of 3–20% by weight based on the swollen mass; and thereafter subjecting the swollen mass to casting, evaporating and water-immersing steps, thus obtaining the film or block of cellulose diacetate aqueous gel; and wherein each step of the process is carried out at room temperature.

2. A process as claimed in claim 1, wherein the formamide added under stirring to said swollen mass is in the range of 3–10% by weight based on the swollen mass.

* * * * *